United States Patent
Ziegler et al.

(10) Patent No.: US 8,604,175 B2
(45) Date of Patent: Dec. 10, 2013

(54) METHOD FOR PURIFYING FSH OR A FSH MUTANT

(75) Inventors: Thierry Ziegler, Leognan (FR); Mara Rossi, Rome (IT); Antonello Datola, Rome (IT); Sabrina Fiumi, Pomezia Roma (IT)

(73) Assignee: Ares Trading S.A., Aubonne (CH)

( * ) Notice: Subject to any disclaimer, the term of this patent is extended or adjusted under 35 U.S.C. 154(b) by 325 days.

(21) Appl. No.: 12/092,006

(22) PCT Filed: Dec. 6, 2006

(86) PCT No.: PCT/EP2006/069396
§ 371 (c)(1),
(2), (4) Date: Aug. 26, 2008

(87) PCT Pub. No.: WO2007/065918
PCT Pub. Date: Jun. 14, 2007

(65) Prior Publication Data
US 2009/0209454 A1    Aug. 20, 2009

Related U.S. Application Data

(60) Provisional application No. 60/835,754, filed on Aug. 4, 2006.

(30) Foreign Application Priority Data

Dec. 9, 2005 (EP) ..................... 05111915
Dec. 9, 2005 (EP) ..................... 05111917

(51) Int. Cl.
*C07K 1/14* (2006.01)
*C07K 1/16* (2006.01)
*C07K 1/22* (2006.01)
*C07K 1/18* (2006.01)
*C07K 1/34* (2006.01)
*C07K 1/36* (2006.01)
*C07K 14/59* (2006.01)

(52) U.S. Cl.
USPC ........... 530/412; 530/395; 530/397; 530/398; 530/414; 530/417; 530/416

(58) Field of Classification Search
None
See application file for complete search history.

(56) References Cited

U.S. PATENT DOCUMENTS

| | | |
|---|---|---|
| 5,338,835 A | 8/1994 | Boime |
| 5,376,567 A | 12/1994 | McCormick et al. |
| 5,405,945 A | 4/1995 | Boime et al. |
| 5,508,261 A | 4/1996 | Moyle et al. |
| 5,567,677 A | 10/1996 | Castensson et al. |
| 5,585,345 A | 12/1996 | Boime |
| 5,883,073 A | 3/1999 | Boime et al. |
| 5,990,288 A | 11/1999 | Musick et al. |
| 6,162,905 A | 12/2000 | Lualdi et al. |
| 7,741,455 B2 | 6/2010 | Valax et al. |
| 2003/0017126 A1 | 1/2003 | Mahadeshwar et al. |
| 2003/0017550 A1 | 1/2003 | Pang |
| 2003/0186893 A1 | 10/2003 | Paradisi et al. |
| 2004/0013644 A1 | 1/2004 | Rasmussen et al. |
| 2004/0115168 A1 | 6/2004 | DeFrees et al. |
| 2005/0186664 A1 | 8/2005 | Rosen et al. |
| 2006/0121568 A1 | 6/2006 | Drapeau et al. |
| 2007/0129295 A1 | 6/2007 | Rossi |
| 2008/0219952 A1 | 9/2008 | Fischer et al. |
| 2008/0280832 A1 | 11/2008 | Muda et al. |

FOREIGN PATENT DOCUMENTS

| | | |
|---|---|---|
| CA | 2399100 | 8/2001 |
| EP | 0475779 A1 | 3/1991 |
| EP | 1 106 623 | 6/2001 |
| EP | 1247818 | 10/2002 |
| EP | 1482031 A1 | 12/2004 |
| GB | 2 055 384 | 3/1981 |
| WO | WO 88/10270 | 12/1988 |
| WO | WO 94/10309 | 5/1994 |
| WO | WO 96/25496 | 8/1996 |
| WO | WO 97/29767 | 2/1997 |
| WO | WO 98/20039 | 5/1998 |
| WO | WO 98/21234 | 5/1998 |
| WO | WO 00/63248 | 10/2000 |
| WO | WO 01/58493 | 8/2001 |
| WO | WO 2004/006756 | 1/2004 |
| WO | WO 2004/050679 | 6/2004 |
| WO | WO 2005/001025 | 1/2005 |
| WO | WO 2005/020934 | 3/2005 |
| WO | WO 2005/063811 | 7/2005 |
| WO | WO 2006/016960 A2 | 2/2006 |
| WO | WO 2006/051070 | 5/2006 |
| WO | WO 2007/084441 | 7/2007 |

OTHER PUBLICATIONS

Na et al., Journal of Microbiology and Biotechnology, Apr. 2005; 15: 395-402.*
Selkirk et al. (From: Methods in Molecular Biology, vol. 244: Protein Purification Protocols: Second Edition, 2004: 125-131.*
Capture; In Chapter 4 of The Amersham Protein Purification Handbook, 18-1132-29, Amersham Pharmacia Biotech AB 1999; pp. 29-36.*

(Continued)

*Primary Examiner* — Bridget E Bunner
*Assistant Examiner* — Christina Borgeest
(74) *Attorney, Agent, or Firm* — Saliwanchik, Lloyd & Eisenschenk

(57) ABSTRACT

The invention relates to a method for purifying a glycoprotein, preferably FSH or a FSH mutant, comprising the steps of subjecting a liquid containing FSH or a FSH mutant to: (1) a dye affinity chromatography; (2) a weak anion exchange chromatography; (3) a hydrophobic interaction chromatography; and (4) a strong anion exchange chromatography; which may be carried out in any order.

13 Claims, No Drawings

(56) References Cited

OTHER PUBLICATIONS

Website at Google Books: books?id=3WhftkdNpxYC&pg=PA19&lpg=PA19&dq=source+15q,+tmae&source=bl&ots=Kxl3l26Ehp&sig=ww91PtRgjuMjr9pyejUNm2yan3E&hl=en&ei=JcqgTJW6CsG78gbu59ykDg&sa=X&oi=book_result&ct=result&resnum=1&sqi=2&ved=0CBIQ6AEwAA#v=onepage&q=source%2015q%2C%20tmae&f=false; p. 19.*

"Protein Liquid Chromatography", from the Journal of Chromatography Library, Elsevier; vol. 61, 2000; edited by Michael Kastner, which was document X on the PTO-892 form mailed Oct. 6, 2010.*

Protein Purification Handbook, 18-1132-29, "Polishing" In Chapter 6 of the Amersham Pharmacia Biotech AB 1999; pp. 29-36.*

Bradford, M.M. "A Rapid and Sensitive Method for the Quantitation of Microgram Quantities of Protein Utilizing the Principle of Protein-Dye Binding", *Analytical Biochemistry*, 1976, pp. 248-254, vol. 72.

Burgues, S. et al. "Subcutaneous self-administration of highly purified follicle stimulating hormone and human chorionic gonadotrophin for the treatment of male hypogonadotrophic hypogonadism", *Human Reproduction*, 1997, pp. 980-986, vol. 12, No. 5.

Chiba, K. et al. "Isolation and Partial Characterization of LH, FSH and TSH from Canine Pituitary Gland", *Endocrine Journal*, 1997, pp. 205-218, vol. 44, No. 2.

Dulley, J.R. et al. "A Simple Technique for Eliminating Interference by Detergents in the Lowry Method of Protein Determination", *Analytical Biochemistry*, 1975, pp. 136-141, vol. 64.

Hartree, E.F. "Determination of Protein: A Modification of the Lowry Method That Gives a Linear Photometric Response", *Analytical Biochemistry*, 1972, pp. 422-427, vol. 48.

Lowry, O.H. et al. "Protein Measurement with the Folin Phenol Reagent", *J. Biol. Chem.*, 1951, pp. 265-275, vol. 193.

Lynch, S.S. et al. "The Extraction and Purification of Human Pituitary Follicle-stimulating hormone and luteinizing hormone", *Acta Endocrinologica*, 1988, pp. 12-19, vol. 288.

Steelman, S.L. et al. "Assay of the Follicle Stimulating Hormone Based on the Augmentation with Human Chorionic Gonadotropin", *Endocrinology*, 1953, pp. 604-616, vol. 53.

Van Hell, H. et al. "Effects of Human Menopausal Gonadotrophin Preparations in Different Bioassay Methods", *Acta Endocrinologica*, 1964, pp. 409-418, vol. 47.

Flack, M. R. et al. "Site-directed Mutagenesis Defines the Individual Roles of the Glycosylation Sites on Follicle-stimulating Hormone" *The Journal of Biological Chemistry*, May 13, 1994, pp. 14015-14020, vol. 269, No. 19.

Na, H. K. et al. "Purification and Characterization of Recombinant Human Follicle Stimulating Hormone Produced by Chinese Hamster Ovary Cells" *Journal of Microbiology and Biotechnology*, 2005, pp. 395-402, vol. 15, No. 2.

Oki, S. et al. "Macrophage Migration Inhibitory Factor (MIF) Produced by a Human T Cell Hybridoma Clone" *Lymphokine and Cytokine Research*, 1991, pp. 273-280, vol. 10, No. 4.

Peyer, C. et al. "Purification and characterization of β-xylosidase from potatoes (*Solanum tuberosum*)" *BBA*, 2004, pp. 27-35, vol. 1672, No. 1, Elsevier Science Publishers.

Ribela, M. T. et al. "Synthesis and chromatographic purification of recombinant human pituitary hormones" *Journal of Chromatography B*, 2003, pp. 285-316, vol. 790, Nos. 1-2.

Santi, D. V. et al. "Purification and Characterization of Recombinant *Pneumocystis carinii* Thymidylate Synthase" *Protein Expression and Purification*, 1991, pp. 350-354, vol. 2.

Soto, A. M. et al. "A Plasma-Borne Specific Inhibitor of the Proliferation of Human Estrogen-Sensitive Breast Tumor Cells (Estrocolyone-I)" *J. Steroid Biochem. Molec. Biol.*, 1992, pp. 703-712, vol. 43, No. 7.

"Source 15 HIC" [Online], Nov. 2002, pp. 2002-2011, *Amersham Biosciences*, XP002437160, Retrieved from the Internet.

Office Action mailed Mar. 18, 2009 in U.S. Appl. No. 10/581,172, filed Feb. 6, 2007.

Tikhomirov, M.M. et al. "High-Performance Liquid Chromatographic Investigation of the Amino Acid, Amino Sugar and Neutral Sugar Content in Glycoproteins",*Journal of Chromatography*, 1978, pp. 197-203, vol. 167.

Altschul, S. F. et al. "Basic Local Alignment Search Tool" *Journal of Molecular Biology*, 1990, pp. 403-410, vol. 215.

Altschul, S. F. et al. "Gapped BLAST and PSI-BLAST: a new generation of protein database search programs" *Nucleic Acids Research*, 1997, pp. 3389-3402, vol. 25, No. 17.

Barber, M. et al. "Fast Atom Bombardment of Solids (F.A.B.): A New Ion Source for Mass Spectrometry" *J.C.S. Chem. Comm.*, 1981, pp. 325-327.

Busslinger, M. et al. "$β^+$ Thalassemia: Aberrant Splicing Results from a Single Point Mutation in an Intron" *Cell*, Dec. 1981, pp. 289-298, vol. 27.

Chernajovsky, Y. et al. "Efficient Constitutive Production of Human Fibroblast Interferon by Hamster Cells Transformed with the IFN-$β_1$ Gene Fused to an SV40 Early Promoter" *DNA*, 1984, pp. 297-308, vol. 3, No. 4.

Chomczynski, P. et al. "Single-Step Method of RNA Isolation by Acid Guanidinium Thiocyanate-Phenol-Chloroform Extraction" *Analytical Biochemistry*, 1987, pp. 156-159, vol. 162.

Conradt, H. et al. "Structure of the Carbohydrate Moiety of Human Interferon-β Secreted by a Recombinant Chinese Hamster Ovary Cell Line" *Journal of Biological Chemistry*, Oct. 25, 1987, pp. 14600-14605, vol. 262, No. 30.

Costello, C. "Time, Life . . . and Mass Spectrometry New Techniques to Address Biological Questions" *Biophysical Chemistry*, 1997, pp. 173-188, vol. 68.

Cummings, R. D. "Structure and Function of the Selectin Ligand PSGL-1" *Brazilian Journal of Medical and Biological Research*, 1999, pp. 519-528, vol. 32, No. 5.

Dell, A. et al. "Glycoprotein Structure Determination by Mass Spectrometry" *Science*, Mar. 23, 2001, pp. 2351-2356, vol. 291.

Derynck, R. et al. "Isolation and Structure of a Human Fibroblast Interferon Gene" *Nature*, Jun. 19, 1980, pp. 542-547, vol. 285.

Devereux, J. et al. "A comprehensive set of sequence analysis programs for the VAX" *Nucleic Acids Research*, 1984, pp. 387-395, vol. 12, No. 1.

Domon, B. et al. "Structure Elucidation of Glycosphingolipids and Gangliosides Using High-Performance Tandem Mass Spectrometry" *Biochemistry*, 1988, pp. 1534-1543, vol. 27.

Fenn, J. et al. "Electrospray Ionization for Mass Spectrometry of Large Biomolecules" *Science*, Oct. 6, 1989, pp. 64-71, vol. 246.

Graham, F. L. et al. "A New Technique for the Assay of Infectivity of Human Adenovirus 5 DNA" *Virology*, 1973, pp. 456-467, vol. 52.

Grantham, R. "Amino Acid Difference Formula to Help Explain Protein Evolution" *Science*, Sep. 6, 1974, pp. 862-864, vol. 185, No. 4154.

Gray, G. "Linkage Analysis Using Reductive Cleavage Method" *Methods in Enzymology*, 1990, pp. 573-587, vol. 193.

Harvey, D. J. "Collision-Induced Fragmentation of Underivatized N-Linked Carbohydrates Ionized by Electrospray" *Journal of Mass Spectrometry*, 2000, pp. 1178-1190, vol. 35.

Hillenkamp, F. et al. "Matrix-Assisted Laser Desorption/Ionization Mass Spectrometry of Biopolymers" *Analytical Chemistry*, Dec. 15, 1991, pp. 1193-1203, vol. 63, No. 24.

Innis, M. et al. "Procedures for Expression, Modification, and Analysis of Human Fibroblast Interferon (IFN-β) Genes in Heterologous Cells" *Methods in Enzymology*, 1986, pp. 397-403, vol. 119.

Kagawa, Y. et al. "Comparative Study of the Asparagine-Linked Sugar Chains of Natural Human Interferon-β1 and Recombinant Human Interferon-β1 Produced by Three Different Mammalian Cells" *Journal of Biological Chemistry*, Nov. 25, 1988, pp. 17508-17515, vol. 263, No. 33.

Kao, F. et al. "Genetics of Somatic Mammalian Cells, VII. Induction and Isolation of Nutritional Mutants in Chinese Hamster Cells" *Proc N.A.S.*, 1968, pp. 1275-1281, vol. 60.

Kaufman, R. et al. "Amplification and Expression of Sequences Cotransfected with a Modular Dihydrofolate Reductase Complementary DNA Gene" *J. Mol. Biol.*, 1982, pp. 601-621, vol. 159.

(56) References Cited

OTHER PUBLICATIONS

Martinez, G. et al. "Protein Salting-Out Method Applied to Genomic DNA Isolation from Fish Whole Blood" *BioTechniques*, Feb. 1998, pp. 238-239, vol. 24, No. 2.
Miyaji, H. et al. "Efficient Expression of Human Beta-Interferon in Namalwa KJM-1 Cells Adapted to Serum-Free Medium by a DHFR Gene Coamplification Method" *Cytotechology*, 1990, pp. 173-180, vol. 4.
Morris, H. et al. "Fab-Mapping of Recombinant-DNA Protein Products" *Biochemical and Biophysical Research Communications*, Nov. 30, 1983, pp. 299-305, vol. 117 No. 1.
Mory, Y et al. "Synthesis of Human Interferon $\beta_1$ in *Escherichia coli* Infected by a Lambda Phage Recombinant Containing a Human Genomic Fragment" *Eur. J. Biochem.*, 1981, pp. 197-202, vol. 120.
Puck, T. et al. "Genetics of Somatic Mammalian Cells, III. Long-Term Cultivation of Euploid Cells From Human and Animal Subjects" *The Journal of Experimental Medicine*, Jul. 24, 1958, pp. 945-959, vol. 108.
Reiser, W. et al. "Recombinant Human Interferon Beta From Mammalian Cell Lines" *Drug Res.*, 1987, pp. 482-485, vol. 37, No. 4.
Runkel, L. et al. "Structural and Functional Differences Between Glycosylated and Non-Glycosylated Forms of Human Interferon-$\beta$ (IFN-$\beta$)" *Pharmaceutical Research*, 1998, pp. 641-649, vol. 15, No. 4.
Smith, T. F. et al. "Identification of Common Molecular Subsequences" *J. Mol. Biol.*, 1981, pp. 195-197, vol. 147.
Smith, T. F. etal. "Comparison of Biosequences" *Advances in Applied Mathematics*, 1981, pp. 482-489, vol. 2.
Tarentino, A. et al. "Deglycosylation of Asparagine-Linked Glycans by Peptide: *N*-Glycosidase F" *Biochemistry*, 1985, pp. 4665-4671, vol. 24, No. 17.
Urlaub, G. et al. "Isolation of Chinese Hamster Cell Mutants Deficient in Dihydrofolate Reductase Activity" *Proc. Natl. Acad. Sci. USA*, Jul. 1980, pp. 4216-4220, vol. 77, No. 7.
Wilm, M. et al. "Analytical Properties of the Nanoelectrospray Ion Source" *Anal. Chem.*, Jan. 1, 1996, pp. 1-8, vol. 68, No. 1.
Yousefi, S. et al. "A Practical Cytopathic Effect/Dye-Uptake Interferon Assay for Routine Use in the Clinical Laboratory" *Brief Scientific Reports*, Jun. 1985, pp. 735-740, vol. 83, No. 6.
Armour, K. L. et al. "Recombinant human IgG molecules lacking FC$\gamma$ receptor I binding and monocyte triggering activities" *Eur. J. Immunol.*, 1999, pp. 2613-2624, vol. 29.
Bodmer, J.-L. et al. "The molecular architecture of the TNF superfamily" *TRENDS in Biochemical Sciences*, Jan. 2002, pp. 19-26, vol. 27, No. 1.
Bossen, C. et al. "Interactions of Tumor Necrosis Factor (TNF) and TNF Receptor Family Members in the Mouse and Human" *The Journal of Biological Chemistry*, May 19, 2006, pp. 13964-13971, vol. 281, No. 20.
Carter, P. J. "Potent antibody therapeutics by design" *Nature*, May 2006, pp. 343-357, vol. 6.
Hinton, P. R. et al. "Engineered Human IgG Antibodies with Longer Serum Half-lives in Primates" *The Journal of Biological Chemistry*, Feb. 20, 2004, pp. 6213-6216, vol. 279, No. 8.
Idusogie, E. E. et al. "Mapping of the C1q Binding Site on Rituxan, a Chimeric Antibody with a Human IgG1 Fc" *The Journal of Immunology*, 2000, pp. 4178-4184, vol. 164.
Idusogie, E. E. et al. "Engineered Antibodies with Increased Activity to Recruit Complement" *The Journal of Immunology*, 2001, pp. 2571-2575, vol. 166.
Knight, E. et al. "Human Fibroblast Interferon" *The Journal of Biological Chemistry*, Apr. 25, 1981, pp. 3609-3611, vol. 256, No. 8.
Locksley, R. M. et al. "The TNF and TNF Receptor Superfamilies: Integrating Mammalian Biology" *Cell*, Feb. 23, 2001, pp. 487-501, vol. 104.
Moore, P. A. et al. "BLyS: Member of the Tumor Necrosis Factor Family and B Lymphocyte Stimulator" *Science*, Jul. 9, 1999, pp. 260-263, vol. 285.
Naismith, J. H. et al. "Modularity in the TNF-receptor family" *TIBS*, Feb. 1998, pp. 74-79, vol. 23.

Novak, A. J. et al. "Expression of BCMA, TACI, and BAFF-R in multiple myeloma: a mechanism for growth and survival" *Blood*, 2004, pp. 689-694, vol. 103.
Shields, R. L. et al. "High Resolution Mapping of the Binding Site on Human IgG1 for Fc$\gamma$R1, Fc$\gamma$RII, Fc$\gamma$RIII, and FcRn and Design of IgG1 Variants with Improved Binding to the Fc$\gamma$R" *The Journal of Biological Chemistry*, Mar. 2, 2001, pp. 6591-6604, vol. 276, No. 9.
Steurer, W. et al. "Ex Vivo Coating of Islet Cell Allografts with Murine CTLA4/Fc Promotes Graft Tolerance" *The Journal of Immunology*, 1995, pp. 1165-1174, vol. 155.
Vaccaro, C. et al. "Engineering the Fc region of immunoglobulin G to modulate in vivo antibody levels" *Nature Biotechnology*, Oct. 2005, pp. 1283-1288, vol. 23, No. 10.
Vlatakis, G. et al. "Dye-Ligand Chromatography for the Resolution and Purification of Restriction Endonucleases" *Applied Biochemistry and Biotechnology*, 1987, pp. 201-212, vol. 15.
Written Opinion in International Application No. PCT/EP2008/064208, Dec. 15, 2008, pp. 1-7.
Denizli, A. et al. "Dye-ligand affinity systems" *J. Biochem. Biophys. Methods*, 2001, pp. 391-416, vol. 49, XP-002466734.
Gross, J. A. et al. "TACI and BCMA are receptors for a TNF homologue implicated in B-cell autoimmune disease" *Nature*, Apr. 27, 2000, pp. 995-999, vol. 404.
Hahne, M. et al. "APRIL, a New Ligand of the Tumor Necrosis Factor Family, Stimulates Tumor Cell Growth" *J. Exp. Med.*, Sep. 21, 1998, pp. 1185-1190, vol. 188, No. 6.
Hymowitz, S. G. et al. "Structures of APRIL-Receptor Complexes: Like BCMA, TACI employs only a single cysteine-rich domain for High Affinity Ligand Binding" *The Journal of Biological Chemistry*, Feb. 25, 2005, pp. 7218-7227, vol. 28, No. 8.
Melchers, F. "Actions of BAFF in B cell maturation and its effects on the development of autoimmune disease" *Ann. Rheum. Dis.*, 2003, pp. 25-27, vol. 62.
Subramanian, S. "Dye-Ligand Affinity Chromatography: The Interaction of Cibacron Blue F3GA With Proteins and Enzymes" *Critical Reviews in Biochemistry*, 1984, pp. 169-205, vol. 16, Issue 2, XP-000646812.
Von Bulow, G.-U. et al. "NF-AT Activation Induced by a CAML-Interacting Member of the Tumor Necrosis Factor Receptor Superfamily" *Science*, Oct. 3, 1997, pp. 138-141, vol. 278.
Emlen, W. "Purification of DNA Antibodies Using Cibacron Blue F3GA Affinity Chromatogrphy" *Journal of Immunological Methods*, 1983, pp. 205-215, vol. 62, XP-002466735.
Xia, X.-Z. et al. "TACI is a TRAF-interacting Receptor for TALL-1, a Tumor Necrosis Factor Family Member Involved in B Cell Regulation" *J. Exp. Med.*, Jul. 3, 2000, pp. 137-143, vol. 192, No. 1.
Written Opinion in International Application No. PCT/EP2008/064210, Jan. 13, 2009, pp. 1-8.
Pending claims in U.S. Appl. No. 12/738,447, filed Apr. 16, 2010.
Pending claims in U.S. Appl. No. 12/738,515, filed Apr. 16, 2010.
Bell, J. et al. "Blue Dextran: Influence on Chromatographic Profile and Immunoreactivity of Human Follicle-Stimulating Hormane (HFSH) (38852)" *Proc. Soc. Exp. Biol. Med.*, 1975, pp. 565-569, vol. 149.
Nomura, K. et al. "Partial purification and characterization of a renotropic fraction from ovine pituitaries" *Proc. Natl. Acad. Sci. USA*, Nov. 1982, pp. 6675-6679, vol. 79.
El Rassi, Z., Handbook of HPLC—Chromatographic Sciences Series, vol. 78, Edited by E. Katz, R. Eksteen, P. Schoenmakers and N. Miller, Marcel Dekker Inc., New York, USA, 1998, pp. 989 ISBN 0-8247-9444, pp. 463-482, Ch. 12, Hydrophobic Interaction Chromatography of Biopolymers.
Miyaji, H. et al. "Expression of human beta-interferon in Namalwa KJM-1 which was adapted to serum-free medium" *Cytotechnology*, 1990, pp. 133-140, vol. 3.
Paty, D. W. et al. "Interferon beta-1b is effective in relapsing-remitting multiple sclerosis" *Neurology*, 1993, pp. 662-667, vol. 43.
ATCC Catalog No. 30-2001, 2002, p. 1.
Bishop, L.A. et al. "Both of the $\beta$-Subunit Carbohydrate Residues of Follicle-Stimulating Hormone Determine the Metabolic Clearance Rate and in Vivo Potency" *Endocrinology*, 1995, pp. 2635-2640, vol. 136, No. 6.

(56) References Cited

OTHER PUBLICATIONS

Chappel, S. et al. "Follicle stimulating hormone and its receptor: future perspectives" *Human Reproduction*, 1998, pp. 18-35 and 47-51, vol. 13, Supplement No. 3.

D'Antonio, M. et al. "Biological characterization of recombinant human follicle stimulating hormone isoforms" *Human Reproduction*, 1999, pp. 1160-1167, vol. 14, No. 5.

Furuhashi, M. et al. "Effect of Additional N-Glycosylation Signal in the N-Terminal Region on Intracellular Function of the Human Gonadotropin α-Subunit" *Endocrine Journal*, Jun. 2003, pp. 245-253, vol. 50, No. 3.

Galway, A. B. et al. "In Vitro and in Vivo Bioactivity of Recombinant Human Follicle-Stimulating Hormone and Partially Deglycosylated Variants Secreted by Transfected Eukaryotic Cell Lines" *Endocrinology*, 1990, pp. 93-100, vol. 127, No. 1.

Grossman, M. et al. "Site-Directed Mutagenesis of Amino Acids 33-44 of the Common α-Subunit Reveals Different Structural Requirements for Heterodimer Expression among the Glycoprotein Hormones and Suggests that Cyclic Adenosine 3',5'-Monophosphate Production and Growth Promotion are Potentially Dissociable Functions of Human Thyrotropin" *Molecular Endocrinology*, 1996, pp. 769-779, vol. 10, No. 6.

Liu, C. et al. "Site-directed Alanine Mutagenesis of Phe[33], Arg[35], and Arg[42]-Ser[43]-Lys[44] in the Human Gonadotropin α-Subunit" *The Journal of Biological Chemistry*, Oct. 15, 1993, pp. 21613-21617, vol. 268, No. 29.

Perlman, S. et al. "Glycosylation of an N-Terminal Extension Prolongs the Half-Life and Increases the in Vivo Activity of Follicle Stimulating Hormone" *Journal of Clinical Endocrinology and Metabolism*, Jul. 2003, pp. 3227-3235, vol. 88, No. 7.

Roth, K.E. et al. "Scanning-alanine mutagenesis of long loop residues 33-53 in follicle stimulating hormone beta subunit" *Molecular and Cellular Endocrinology*, 1995, pp. 143-149, vol. 109.

Valove, F.M. et al. "Receptor Binding and Signal Transduction are Dissociable Functions Requiring Different Sites on Follicle Stimulating Hormone" *Endocrinology*, 1994, pp. 2657-2661, vol. 135, No. 6.

Weenen, C. et al. "Long-Acting Follicle-Stimulating Hormone Analogs Containing N-Linked Glycosylation Exhibited Increased Bioactivity Compared with O-Linked Analogs in Female Rats" *Journal of Clinical Endocrinology and Metabolism*, Oct. 2004, pp. 5204-5212, vol. 89, No. 10.

Yoo, J. et al. "COOH-terminal Amino Acids of the α Subunit Play Common and Different Roles in Human *Choriogonadotropin and Follitropin*" *The Journal of Biological Chemistry*, Jun. 25, 1993, pp. 13034-13042, vol. 268, No. 18.

Database Geneseq [Online], Jan. 29, 2002, "Human FSH-alpha subunit mutant D3N/Q5T", XP-002439754, Database Accession No. AAM51736, p. 1.

Database Geneseq [Online], Jan. 29, 2002, "Human FSH-alpha subunit mutant D3N/Q5S", XP-002439755, Database Accession No. AAM51735, p. 1.

Office Action mailed Oct. 18, 2012 in U.S. Appl. No. 13/159,864, filed Jun. 14, 2011.

* cited by examiner

SEQUENCE LISTING

```
<160> NUMBER OF SEQ ID NOS: 2

<210> SEQ ID NO 1
<211> LENGTH: 92
<212> TYPE: PRT
<213> ORGANISM: Artificial
<220> FEATURE:
<223> OTHER INFORMATION: alpha subunit mutant H83N

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys Asn Cys Ser Thr Cys Tyr Tyr His Lys Ser
                85                  90

<210> SEQ ID NO 2
<211> LENGTH: 111
<212> TYPE: PRT
<213> ORGANISM: Artificial
<220> FEATURE:
<223> OTHER INFORMATION: beta subunit mutant E 55N/V57T

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Asn Leu Thr Tyr Glu Thr Val Arg Val Pro
    50                  55                  60

Gly Cys Ala His His Ala Asp Ser Leu Tyr Thr Tyr Pro Val Ala Thr
65                  70                  75                  80
```

```
Gln Cys His Cys Gly Lys Cys Asp Ser Asp Ser Thr Asp Cys Thr Val
            85                  90                  95

Arg Gly Leu Gly Pro Ser Tyr Cys Ser Phe Gly Glu Met Lys Glu
            100             105                 110
```

METHOD FOR PURIFYING FSH OR A FSH MUTANT

CROSS-REFERENCE TO RELATED APPLICATION

This application is the U.S. national stage application of International Patent Application No. PCT/EP2006/069396, filed Dec. 6, 2006, which claims the benefit of U.S. Provisional Patent Application No. 60/835,754, filed Aug. 4, 2006, the disclosures of which are hereby incorporated by reference in their entireties, including all figures, tables and amino acid or nucleic acid sequences.

FIELD OF INVENTION

The invention relates to the purification of a glycoprotein, preferably a follicle stimulating hormone (FSH) or of a mutant thereof.

BACKGROUND OF THE INVENTION

Follicle-stimulating hormone (FSH) is a protein falling into the class of gonadotrophins. FSH is used in the treatment of infertility and reproductive disorders in both female and male patients.

In nature, FSH is produced by the pituitary gland. For pharmaceutical use, FSH may be produced recombinantly (rFSH), or it may be isolated from the urine of postmenopausal females (uFSH).

FSH is used in female patients in ovulation induction (OI) and in controlled ovarian hyperstimulation (COH) for assisted reproductive technologies (ART). In a typical treatment regimen for ovulation induction, a patient is administered daily injections of FSH or a variant (about 75 to 300 IU FSH/day) for a period of from about 6 to about 12 days. In a typical treatment regimen for controlled ovarian hyperstimulation, a patient is administered daily injections of FSH or a variant (about 150-600 IU FSH/day) for a period of from about 6 to about 12 days.

FSH is also used to induce spermatogenesis in men suffering from oligospermia. A regimen using 150 IU FSH 3 times weekly in combination with 2'500 IU hCG twice weekly has been successful in achieving an improvement in sperm count in men suffering from hypogonadotrophic hypogonadism [Burgues et al.; *Subcutaneous self-administration of highly purified follicle stimulating hormone and human chorionic gonadotrophin for the treatment of male hypogonadotrophic hypogonadism. Spanish Collaborative Group on Male Hypogonadotrophic Hypogonadism; Hum. Reprod.;* 1997, 12, 980-6].

FSH agonists/FSH mutants with increased half-lives have been developed by fusing the carboxyterminal peptide of hCG (CTP) to native recombinant human FSH (rhFSH). The CTP moiety consists of amino acids 112-118 to 145 with four O-linked glycosylation sites located at positions 121, 127, 132 and 138. U.S. Pat. No. 5,338,835 and U.S. Pat. No. 5,585,345 disclose a modified FSH β-subunit extended at the C-terminal Glu with the CTP moiety of hCG. The resulting modified analogue is stated to have the biological activity of native FSH, but a prolonged circulating half-life. U.S. Pat. No. 5,405,945 discloses that the carboxy terminal portion of the hCG beta-subunit or a variant thereof has significant effects on the clearance of CG, FSH, and LH.

U.S. Pat. No. 5,883,073 discloses single-chain proteins comprised of two α-subunits with agonist or antagonist activity for CG, TSH, LH and FSH. U.S. Pat. No. 5,508,261 discloses heterodimeric polypeptides having binding affinity to LH and FSH receptors comprising a glycoprotein hormone α-subunit and a non-naturally occurring β-subunit polypeptide, wherein the β-subunit polypeptide is a chain of amino acids comprising four joined subsequences, each of which is selected from a list of specific sequences. Klein et al. (2003) discloses a single chain analogue of FSH with an increased half-life, wherein the α- and beta-subunits are linked by an oligopeptide containing two N-linked glycosylation sites.

WO 01/58493 discloses 77 mutations that may be made in the α-subunit of FSH and 51 mutations that may be made in the beta-subunit of FSH in an attempt to improve the in vivo half-life of FSH. WO 01/58493 discloses that the mutant α- and β-subunits may be used individually (1 additional glycosylation site) or in combination (2 additional glycosylation sites). The 128 candidate mutants were identified by using 50 models of the 3D structure of FSH that were generated based solely on the structure of hCG and a sequence alignment of FSH and hCG despite only 32% identity between the beta-subunits of hCG and FSH. WO 01/58493 does not disclose the production or testing of any α- or β-subunits of FSH where a glycosylation site was introduced by site directed mutagenesis.

WO 05/020934 discloses the FSH mutant GM1, with mutations in both the alpha- and beta-subunits of FSH, including a mutation at H83N of the alpha-subunit and a double mutation at E55N/V57T of the beta-subunit.

Because of the importance of FSH in the treatment of fertility disorders, the provision of FSH or mutants of FSH of high purity and high specific activity is desirable. FSH treatment requires repeated injections. Highly purified FSH preparations can be administered subcutaneously, permitting self-administration by the patient, thus increasing patient convenience and compliance.

Lynch et al. [The extraction and purification of human pituitary follicle-stimulating hormone and luteinising hormone; *Acta Endocrinologica,* 1988, 288, 12-19] describe a method for purifying human pituitary FSH. The method involves anion and cation exchange chromatography, immunoaffinity extraction and size exclusion chromatography. The method is said to result in pituitary FSH having a specific activity of 4,990 IU (immunoassay)/mg, with 16 IU/mg of LH. Protein content was determined either by dry weight or in solution by absorption at 280 nm (assuming that $A^{280}_{1cm}$ for 1 g/l is equal to 1).

WO 98/20039 (IBSA Institut Biochimique SA) describes a process for the purification of human urinary FSH starting with urinary extracts called human menopausal gonadotrophins (hMG). The process uses ion-exchange chromatography on weakly basic anionic exchange resins of the DEAE type followed by affinity chromatography on resin having an anthraquinone derivative as a ligand. The process is said to yield urinary FSH free from LH and having a specific activity of 6,870 IU (immuno-assay)/mg. Protein content was determined by assuming that a water solution of 1 mg/ml of protein has an optical density of 0.62 at 277 nm, in quartz cuvettes with a 1 cm path length.

WO 00/63248 (Instituto Massone SA) describes a process for the purification of gonadotrophins, including FSH, from human urine. The process involves the following steps: ion exchange chromatography with a strong cationic resin of the type sulphopropyl, ion exchange chromatography with a strong anionic resin, and hydrophobic interaction chromatography (HIC). A FSH preparation having a specific activity of 8,400 IU/mg (Steelman-Pohley method: *Assay of the follicle stimulating hormone based on the augmentation with human chorionic gonadotrophin; Endocrinology;* 1953, 53, 604-616) and less than 1 IU LH (rat seminal vesicle weight gain method: Van Hell H, Matthijsen R & G A Overbeek; *Acta Endocrinol,* 1964, 47, 409) biological activity per 75 IU FSH is reportedly obtained. Protein content was performed by the Lowry method [O. H. Lowry et al., *J. Biol. Chem.,* 1951, 193, 265].

U.S. Pat. No. 5,990,288 (Musick et al.) describes a method for purifying FSH from biological samples, such as human pituitary glands or human post-menopausal urine. The process uses cation exchange chromatography on Fractogel EMD $SO_3$-650M, followed by dye affinity chromatography on Mimetic Orange 1 resin, followed by a step of hydrophobic interaction chromatography on Bakerbond Wide Pore HI-Propyl resin. The process is said to result in human pituitary FSH having a specific activity of 7,066 IU (immunoassay)/mg and less than 1 IU (immunoassay)/mg of LH, and a urinary FSH having a specific activity of 6,298 IU (immunoassay)/mg and less than 3 IU (immunoassay)/mg of LH. Protein content was determined by absorption at 280 nm (assuming that $A^{280}_{1cm}$ for 1 g/l is equal to 1).

Chiba et al. [Isolation and partial characterisation of LH, FSH and TSH from canine pituitary gland; *Endocrinol. J.,* 1997, 44, 205-218] describe a technique for purifying canine pituitary gonadotrophins, including FSH, using Concanavalin (Con) A affinity chromatography, hydrophobic interaction chromatography (HIC) and immobilized metal ion chromatography with $Cu^{++}$. The resulting FSH is reported to have a specific activity of 2.17 IU/g protein using a radioreceptor assay for FSH for measuring biological activity and the Bio-Rad protein assay kit (BioRad Laboratories CA USA) for determining protein content.

WO 88/10270 (Instituto di Ricerca Cesare Serono SPA) describes a method for purifying human FSH from urine. The process involves immunochromatography with FSH-specific immobilized monoclonal antibodies bound to Sepharose 4B by divinyl sulphone, followed by reverse phase HPLC. The resulting FSH is free of LH and other urinary proteins and has a specific activity of 6,200 IU/mg of lyophilised powder (Steelman-Pohley method). The preparation was the first FSH preparation to be suitable for subcutaneous administration, due to its purity.

SUMMARY OF THE INVENTION

In a first aspect, the invention provides a method for purifying a glycoprotein, preferably FSH or a FSH mutant.

In a second aspect, the invention provides a method for purifying a FSH mutant having an alpha subunit according to SEQ ID NO 1 and a beta subunit according to SEQ ID NO 2.

The method comprises subjecting a liquid containing said glycoprotein, preferably said FSH or FSH mutant, to the following chromatographic steps
(1) dye affinity chromatography;
(2) weak anion exchange chromatography;
(3) hydrophobic interaction chromatography;
(4) strong anion exchange chromatography.

The chromatographic steps may be carried out in any order.

The FSH mutant according to the present invention may preferably comprise one or more of the following mutations compared to wild-type FSH:

D3N and/or H83N in the alpha-subunit, and/or
E55N and/or V57T in the beta-subunit.

The FSH mutants may also comprise amino acid inserts compared to wildtype FSH. In preferred embodiments four-amino acid sequences such as GNFT or GNRT are inserted between amino acids 3 and 4 of the wild-type FSH alpha-subunit.

In a preferred embodiment, the FSH mutants comprise a D3N mutation in the alpha-subunit and a double mutation E55NN57T in the beta-subunit.

In another preferred embodiment, the FSH mutants comprise a GNFT insert between amino acids 3 and 4 of the wild-type FSH alpha-subunit and a double mutation E55NN57T in the beta-subunit.

In another preferred embodiment, the FSH mutants comprise a GNRT insert between amino acids 3 and 4 of the wild-type FSH alpha-subunit and a double mutation E55NN57T in the beta-subunit.

In another preferred embodiment, the FSH mutants comprise a H83N mutation in the alpha-subunit and a double mutation E55N/V57T in the beta-subunit.

A particularly preferred FSH mutant according to the present invention is the one described in WO 2005/020934, referred to as GM1, wherein the FSH alpha-subunit comprises the sequence of SEQ ID NO. 1, and wherein the FSH beta-subunit comprises the sequence of SEQ ID NO. 2.

In the wild type FSH there are 4 N glycosylation sites, 2 each within the alpha (N52 & N78) and the beta (N7 & N24) subunit.

The mutant FSH may be N-glycosylated at 0, 1, 2, 3, 4, 5 or 6 asparagine residues of said mutant FSH. N83 of the mutant alpha-subunit may be glycosylated, further to the glycosylation sites of wild-type FSH. N55 of the mutant beta-subunit may be glycosylated, further to the glycosylation sites of wild type FSH.

In a preferred embodiment the FSH mutant has an FSH alpha-subunit comprising the sequence of SEQ ID NO. 1, and an FSH beta-subunit comprising the sequence of SEQ ID NO. 2, wherein N52 and N78 of the alpha-subunit are glycosylated and further N7 and N24 of the beta-subunit are glycosylated. This FSH mutant is referred to herein as GM1 with diglycosylated beta-subunit.

In a most preferred embodiment the FSH mutant has an FSH alpha-subunit comprising the sequence of SEQ ID NO. 1, and an FSH beta-subunit comprising the sequence of SEQ ID NO. 2, wherein N52 and N78 of the alpha-subunit are glycosylated and further N7, N24 and N55 of the beta-subunit are glycosylated. This FSH mutant is referred to as GM1 with triglycosylated beta-subunit.

A third aspect of the present invention relates to a method of enriching a sample of FSH or FSH mutants for proteins with tri-glycosylated beta-subunits comprising the step of subjecting the sample to hydrophobic interaction chromatography.

Preferably hydrophobic interaction chromatography is performed on a Source 15 or an analogous column.

Preferably, the FSH mutant is GM1.

A fourth aspect of the present invention consists in a FSH mutant with an alpha subunit according to SEQ ID NO 1 and a beta subunit according to SEQ ID NO 2 whereby said FSH mutant has a specific bioactivity of between 11.000 and 17.000 IU/mg.

A fifth aspect of the present invention consists in a pharmaceutical composition comprising a glycoprotein, preferably FSH or a FSH mutant having an alpha subunit according to SEQ ID NO 1 and a beta subunit according to SEQ ID NO 2, obtained by the method of the present invention as well as a pharmaceutically acceptable excipient.

A sixth aspect of the present invention consists in the use of FSH or a FSH mutant having an alpha subunit according to SEQ ID NO 1 and a beta subunit according to SEQ ID NO 2 obtained by the method of the present invention for the preparation of a medicament for the treatment of fertility disorders.

In one embodiment, the FSH or FSH mutant is obtained by recombinant means.

ABBREVIATIONS

The following abbreviations are used in the description of the invention:
DF: diafiltration
FSH: follicle stimulating hormone;
r-FSH: recombinant FSH;
hFSH: human FSH;
r-hFSH: recombinant human FSH
BV: Bed volume
DEAE: diethylaminoethyl
ELISA: enzyme linked immunoassay
DAC: dye affinity chromatography
OD: optical density
HIC: Hydrophobic interaction chromatography
HPLC: high performance liquid chromatography
IRMA: immunoradiometric assay
KD or kD: kiloDalton
HCP: host cell protein, proteins arising from the host cell used for expression of FSH
IPC: In process controls
IEF: isoelectric focussing
PES: polyethersulphone
RP-HPLC: reverse phase high performance liquid chromatography
Q FF: anion exchange on Q Sepharose FF
RT: Room Temperature
UF: ultrafiltration
WFI: water for injection

DETAILED DESCRIPTION OF THE INVENTION

The invention provides a method for purifying a glycoprotein, preferably a FSH or a FSH mutant.

In particular, the invention provides a method for purifying a FSH mutant comprising an alpha subunit according to SEQ ID NO 1 and a beta subunit according to SEQ ID NO 2.

In another embodiment, the glycoprotein is LH or hCG. In still another embodiment, the glycoprotein is an interferon, e.g. interferon beta.

Preferably, the method comprises subjecting a liquid containing said glycoprotein, preferably FSH or said FSH mutant to the following chromatographic steps:
(1) dye affinity chromatography;
(2) weak anion exchange chromatography;
(3) hydrophobic interaction chromatography;
(4) strong anion exchange chromatography;
The chromatographic steps may be carried out in any order.

The purification method of the invention affords a bulk of the glycoprotein, preferably the FSH or FSH mutant, of high purity which may then be formulated to the final medicament. It has the advantage of affording a high degree of purity without using immunoaffinity chromatography. The crude FSH or FSH mutant which forms the starting material for the purification according to the present invention consists in cell culture harvests containing the FSH or FSH mutant.

In a preferred embodiment, an antioxidant or a free amino acid or dipeptide with antioxidant and scavenging effect is included in some or all of the steps of the purification method according to the present invention. More precisely, the antioxidant is present in any of the buffers used to purify and/or concentrate and/or filter the FSH mutant. The antioxidant prevents oxidation of the FSH or FSH mutant during processing. A preferred antioxidant is L-methionine. Preferably, L-methionine is used at a concentration of at or about 10-100 mM. Further examples of an antioxidant include t-butyl-4-methoxy-phenol, 2,6-bis(1,1-dimethylethyl)-4-methyl phenol; potassium or sodium bimeta-bisulfite, sodium bisulfite. Examples of free amino acid and dipeptide with antioxidant and scavenging effect are histidine, taurine, glycine, alanine, carnosine, anserine, 1-methylhistidine or combinations thereof.

Typically, the starting material is clarified first and then optionally concentrated (e.g. by using ultrafiltration) and/or buffer exchanged (e.g. through a diafiltration step) prior to being captured on the first chromatographic step.

In the steps of chromatography, polymer-based and agarose-based resins may be used. It is also possible to use membrane chromatography, in which the resin is replaced with a functionalised membrane.

The 4 purification steps of the present invention are in the following outlined more in detail.

The Dye Affinity Chromatography Step (1)

The method of the invention involves a step of dye affinity chromatography (1). In a preferred embodiment, the step of dye affinity chromatography is carried out using a resin having as an immobilised ligand a dye compound which is well known to a person skilled in the art, i.e. Cibacron Blue F3G-A. The term "immobilized" is well understood by a person skilled in the art and means that the ligand is derivatised in the sense that it is chemically linked to the resin. A particularly preferred resin is Blue Sepharose FF (obtainable from GE Biosciences Inc.). The technical features of Blue Sepharose FF are as follows

| TECHNICAL SPECIFICATIONS | |
| --- | --- |
| Ligand | Cibacron Blue F3G-A |
| Ligand coupling method | Triazine coupling |
| Binding capacity | ≈18 mg human serum albumin/ml drained gel |
| Matrix | Highly cross-linked agarose, 6% |
| Exclusion limit ($M_r$) | $4 \times 10^6$ |
| Particle size range | 45-165 μm |
| Linear flow rate* | ≈750 cm/h |
| Ligand density | ≈7 μmol Cibacron Blue/ml medium |
| pH stability | 4-12 (long term), 3-13 (short term) |
| Chemical stability | 40° C. for 7 days in: 70% ethanol, 6 M guanidine hydrochloride, 8 M urea |

It is understood that the method may be performed with alternate resins, having similar characteristics. Examples of alternative resins include: Toyopearl AF-blue-HC-650M (Tosoh Bioscience), Blue Cellthru BigBead (Sterogene), SwellGel Blue (Pierce), Cibachrome blue 3GA-agarose 100 (Sigma), Affi-Gel Blue (BioRad), Econo-Pac blue cartridges (Bio-Rad), Blue sepharose HP (Amersham), Cibacron Blue 3GA (Sigma).

Elution in the step of immobilised dye affinity chromatography should preferably be carried out using a buffer of phosphate, particularly preferably ammonium hydroxide. The pH of the eluent should preferably be at or about 9.0 to at or about 13, more preferably at or about 10 to at or about 12, particularly preferably at or about 11-12. Alternate buffers appropriate for maintaining a pH of about 11.8 include the following: Ammonium bicarbonate.

In a particularly preferred embodiment, the product-contacting buffers for the step of dye affinity chromatography (equilibration and wash) contain an antioxidant, such as L-methionine. Further examples of an antioxidant include t-butyl-4-methoxyphenol, 2,6-bis(1,1-dimethylethyl)-4-methyl phenol; potassium or sodium bimetabisulfite, sodium bisulfite.

The Weak Anion-Exchange Chromatography Step (2)

The method of the invention also comprises a step of a weak anion-exchange chromatography (2). A preferred resin is DEAE Sepharose FF (obtainable GE Biosciences), or a resin having similar characteristics. Alternatively the step of the weak anion-exchange chromatography may be carried out on Fractogel DEAE (Merck KgaA), Toyopearl DEAE 650M (Tosoh Biosep Inc.). The weak anion exchange chromatography step (2) is preferably carried out using an ammonium acetate buffer at a pH of at or about 7.5 to 9.5.

The Hydrophobic Interaction Chromatography Step (3)

The method also involves a step of hydrophobic interaction chromatography (3). In a preferred embodiment, the hydrophobic interaction chromatography is carried out with a resin such as Toyopearl Butyl 650M (obtainable from Tosoh Biosep Inc.).

It is understood that step (3) may be performed using alternate resins, having similar characteristics. Alternative resins that may be used are as follows: Phenyl Sepharose 6 Fast Flow (low sub); Phenyl Sepharose 6 Fast Flow (high sub); Butyl Sepharose 4 Fast Flow; Octyl Sepharose 4 Fast Flow; Phenyl Sepharose High Performance; SOURCE 15ETH; SOURCE 15ISO; SOURCE 15PHE all from GE Biosciences (800) 526-3593; (see www.amershambiosciences.com). Still further resins are: Hydrocell C3 or C4; Hydrocell Phenyl from BioChrom Labs Inc. (812) 234-2558; (see www.biochrom.com)

Binding on the HIC resin is achieved in a buffer with a high conductivity, obtained through the addition of salt (NaCl, $(NH_4)_2SO_4$ or $Na_2SO_4$ for example). Elution in the step of hydrophobic interaction chromatography is preferably carried out by reducing the conductivity of the mobile phase (reducing salt concentration), using a buffer having a pH at or about 6 to at or about 8, more preferably at or about 6.5 to at or about 7.5, most preferably at or about 7). A particularly preferred system contains sodium phosphate for buffering preferably at a pH of at or about 7, and ammonium sulfate. Alternative buffers are mentioned above.

In a particularly preferred embodiment, the product-contacting buffers for the step (3) of HIC (equilibration, wash, elution) contain an antioxidant, such as L-methionine. Alternative antioxidants are mentioned above.

The Strong Anion-Exchange Chromatography Step (4)

The method of the invention also comprises a second step of anion-exchange chromatography (4), which is performed on a strong anion exchange resin. A preferred resin is Fractogel EMD TMAE HICAP (obtainable from Merck KGaA, Darmstadt Germany).

| | |
|---|---|
| Support | Fractogel ® EMD TMAE |
| Cat. No. | 1.16887 |
| Particle size S-type | 20-40 μm |
| Type of chromatography | ion-exchange chromatography |
| Functional group | trimethylaminoethyl group (Q-type) |
| Monomer structure | $CH_2=CH-CONH-(CH_2)_2N + (CH_3)_3$ |
| Protein binding capacity | 120 mg BSA/ml of gel |
| pH stability range | pH 2 up to pH 12 |
| pK value | >13 |
| Elution conditions | high salt concentrations |
| Pressure limit (bed: 150 × 10 mm) | 20 bar (pressure drop along the column) |
| Working temperature | 4° C. to room temperature |
| Preservative | 20% ethanol |
| Ready to use cartridge | 50-10 mm |
| Bulk material S-types | 100 ml; 500 ml |
| Linear flow rate | 1.27-6.35 cm/min |

Alternatively the second step of anion-exchange chromatography may be carried out on Q Sepharose FF having the following characteristics:

| | |
|---|---|
| Type of ion exchanger: | Strong anion |
| Total capacity (mmol/ml): | 0.18-0.25 |
| Exclusion limit (globular proteins): | $4 \times 10^6$ |
| Bead form: | Spherical, diameter 45-165 μm |
| Bead structure: | Cross-linked agarose, 6% |
| Operational pH stability: | 2-12 |
| Cleaning pH stability: | 1-14 |
| Linear flow rate at 25° C. 1 bar 15 cm bed height, XK 50/30 column: | 400-700 cm/h |

The second step of anion-exchange chromatography is preferably carried out using a buffer having a mildly alkaline pH (e.g. at or about 7.2 to at or about 9.0, or at or about 8.0 to at or about 9.0, most preferably at or about 8.5). Suitable buffers include, for example borate buffer, triethanolamine/iminodiacetic acid Tris, ammonium acetate, tricine, bicine, TES, HEPES, TAPS. Most preferred is borate buffer, at a pH of at or about 8.5. Elution from the anion-exchange resin is achieved by increasing the conductivity of the mobile phase through the addition of salt, preferably NaCl. In a particularly preferred embodiment the product-contacting buffers for the anion-exchange chromatography (equilibration, wash, elution) contain an antioxidant, preferably L-methionine. Alternative antioxidants are mentioned above.

Optional Purification Step (0)—Capture Step

Prior to the step of dye affinity chromatography (1), it may be desirable to carry out a capture step, in order to remove the crudest impurities. The capture step is preferably carried out using a Q Sepharose Fast Flow (GE Biosciences) preferably carried out using a buffer having a mildly alkaline pH (e.g. at or about 6.0 to at or about 9.0, or at or about 6.5 to at or about 8.5, most preferably at or about 7.0). Suitable buffers include, for example borate buffer, triethanolamine/iminodiacetic acid Tris, ammonium acetate, tricine, bicine, TES, HEPES, TAPS. Most preferred is borate buffer, at a pH of at or about 7.0. Elution from the anion-exchange resin is achieved by increasing the conductivity of the mobile phase through the addition of salt, preferably NaCl. In a particularly preferred embodiment the product-contacting buffers for the anion-exchange chromatography (equilibration, wash, elution) contain an antioxidant, preferably L-methionine. Alternative antioxidants are mentioned above.

Optional Further Purification Step (3Bis)—Ultrafiltration/Diafiltration

Prior to the step of the second ion exchange chromatography (4), it may be desirable to carry out a step of ultrafiltration (3bis), in order to concentrate the crude FSH or FSH mutant. The ultrafiltration (or diafiltration) is preferably carried out using a membrane having a cut-off of at or about 3-10 kD, most preferably at or about 8 kD.

Optional Further Purification Step (5)—Nanofiltration

It may be desirable to subject the FSH sample to a step of nanofiltration, in particular as a virus clearance step; i.e. to reduce the risk of contamination of the FSH preparation with viruses or virus-like particles originating from the cell culture.

Nanofiltration may be done at any stage of the purification process, however, it is particularly preferred to carry out nanofiltration after the $2^{nd}$ step of ion exchange chromatography. Nanofiltration may be performed more than one time, for example it may be performed twice.

In a particularly preferred embodiment, the following steps are carried out in the order shown below:
- (0) capture step (preferably using a Q SFF column);
- (1) dye affinity chromatography (preferably using a Blue Sepharose FF column);
- (2) weak anion-exchange chromatography (preferably using a DEAE Sepharose FF column);
- (3) hydrophobic interaction chromatography (HIC) (preferably using a Butyl 650M column);
- (3bis) ultrafiltration (preferably with a membrane having a cut-off of 8 kD);
- (4) anion-exchange chromatography on a strongly basic anion exchange resin (preferably using a TMAE hicap resin);
- (5) nanofiltration The advantage of the present invention is that the purification method is devoid of a cost intensive immuno-affinity chromatography step and provides anyhow a high degree of glycoprotein purity and specific bioactivity. Also, the purified glycoprotein, preferably the FSH or FSH mutant of the present invention, does not contain undesired impurities added by the immuno affinity chromatography (e.g. immunoglobulins leached from the resin)

Samples of glycoproteins, preferably FSH or FSH mutants, which have been subjected to at least steps (1) to (4) and optionally (0), (3bis) and/or (5) are considered as pure.

Hydrophobic Interaction Chromatography Step

A most preferred FSH mutant according to this invention has an FSH alpha-subunit comprising the sequence of SEQ ID NO. 1, and an FSH beta-subunit comprising the sequence of SEQ ID NO. 2, wherein N52 and N78 of the alpha-subunit are glycosylated and further N7, N24 and N55 of the beta-subunit are glycosylated. This FSH mutant is referred to as GM1 with triglycosylated beta-subunit.

However, depending on the cell line chosen for recombinant production of GM1, the N55 position of the beta-subunit may be only partially glycosylated. When produced in CHO (Chinese hamster ovary) cells, a common cell line for the production of FSH and its mutants, only about 40% of GM1 proteins have a tri-glycosylated beta subunit.

As GM1 with tri-glycosylated beta subunit has a higher specific bioactivity than GM1 with di-glycosylated beta subunit, there is a need for a process to accumulate or enrich the proteins with tri-glycosylated beta subunit.

It has now been found that a sample of FSH or FSH mutants may be enriched for proteins with a tri-glycosylated beta-subunit by subjecting it to a hydrophobic interaction column.

In one embodiment the invention therefore relates to a method of enriching a sample of FSH or FSH mutants for proteins with tri-glycosylated beta-subunits comprising the step of subjecting the sample to hydrophobic interaction chromatography. Preferably hydrophobic interaction chromatography is performed on a Source 15 or an analogous column.

It is thus desirable to carry out a hydrophobic interaction chromatography step in particular by using a Source 15 HIC column (from Amersham; defined as a Source 15 resolutive bead of 15 μM diameter) having the following characteristics

| | |
|---|---|
| Support | Source 15 PHE |
| Cat. No. | 17-0147 |
| Particle size S-type | 15 μm |
| Type of chromatography | Hydrophobic Interaction chromatography |
| Functional group | Phenyl |
| Monomer structure | R—O—CH2—CHOH—CH2—O—CH2—CHOH—CH2—O—C6H5 |
| Protein binding capacity | 25 mg BSA/ml of gel |
| pH stability range | pH 2 up to pH 12 |
| pK value | NA |
| Elution conditions | Low salt concentrations, preferably conductivity is 105 ± 2 mS/cm. |
| Pressure limit (bed height: 30 mm) | 14 bar (pressure drop along the column) |
| Working temperature | 4° C. to 40° C. |
| Preservative | 20% ethanol |
| Ready to use cartridge | 5/50-100-150 mm and 10/50-100-150 mm |
| Bulk material S-types | 100 ml; 1 L |
| Linear flow rate | 2.5-15 cm/min |

Columns, which are considered as analogous to the Source 15 HIC column, have the following characteristics: They allow high resolution, have small beads, large pore size and are hydrophilic. Small bead preferably means a size between about 15 to about 40 μm. Large pore size preferably means pore sizes of about 750 to about 1000 Angstrom. Preferably these columns are based on polymer-based resins, which are derivatized with a hydrophobic interaction functional ligand, optionally through linkers of various sizes up to long polymers. Polymer-based resins preferably comprise metacrylate, polystyrene and divinylbenzene resins. Hydrophobic interaction functional ligands preferably comprise ether, propyl, polypropylene glycol, isopropyl, phenyl, butyl and hexyl. Preferred HIC columns used as analogues for the Source 15 column are:
- Fractogel phenyl type S (from Merck)
- TSK gel phenyl 5PW (from Tosoh Biosciences)
- All hydrophobic resins Type 'S' from Merck
- All hydrophobic resins TSK from Tosoh Biosciences In one embodiment—where the protein is a FSH mutant existing in different glycosylation forms—this step provides for an enrichment of the higher glycosylated form. Specifically, using a Source 15 HIC or an analogous column provides for an enrichment of the FSH mutant wherein the beta subunit is e.g. triglycosylated rather than diglycosylated.

In a preferred embodiment, the enrichment step is performed on a pure sample of FSH or FSH mutants, i.e. the sample had previously been subjected to steps (1) to (4), and optionally (O), (3bis) and/or (5) as defined above. However, the sample of FSH or FSH mutants may also have been subjected to a different purification process.

In a preferred embodiment, the present invention thus relates to a method comprising the steps in the order:
(0) capture step;
(1) dye affinity chromatography;
(2) weak anion-exchange chromatography;
(3) hydrophobic interaction chromatography (HIC);
(3bis) ultrafiltration;
(4) strong anion exchange chromatography;
(5) nanofiltration;
(6) hydrophobic interaction chromatography (HIC).

In one embodiment, the enrichment step (6) alone or combined with previous purification steps provides for a final product of the FSH mutant with an alpha-subunit comprising the sequence of SEQ ID NO. 1, and with a FSH beta-subunit comprising the sequence of SEQ ID NO. 2, with the following glycosylation ratio:

| | |
|---|---|
| FSH mutant having a triglycosylated beta subunit | about 70-80% |
| FSH mutant having a diglycosylated beta subunit | about 20-30% |

The ratio of FSH mutant wherein the triglycosylated beta-subunit is present is thus increased compared to a sample without performing the enrichment step in which the ratio is as follows:

| | |
|---|---|
| FSH mutant having a triglycosylated beta subunit | 30-40% |
| FSH mutant having a diglycosylated beta subunit | 70-60%. |

The present invention also relates to a sample of FSH mutants obtainable by the above enrichment step.

FSH mutants having an alpha subunit according to SEQ ID NO 1 and a beta-subunit according to SEQ ID NO 2 with tri-glycosylated beta subunits have higher specific bioactivities than those mutants with di-glycosylated beta-subunits.

In one embodiment of the present invention a FSH mutant having an alpha subunit according to SEQ ID NO 1 and a beta-subunit according to SEQ ID NO 2 and having a specific bioactivity of between 11'000 and 17'000 IU/mg is obtained.

Such mutants, whether obtained by any of the preceding methods or by any other method, are also encompassed by this invention.

Preferably the sample of FSH mutant has a specific bioactivity of between 12,000 and 16,000 IU/mg and more preferably of about 15,000 IU/mg, wherein biological activity is measured by the Steelman-Pohley bioassay and protein content is measured by SE-HPLC.

Preferably the sample of FSH mutant contains at least 60%, preferably at least 70%-80%, more preferably at least 90% tri-glycosylated beta-subunits.

Storage/Lyophilisation

The liquid composition resulting from the purification process as described above and containing purified glycoprotein, preferably FSH or FSH mutant, may be frozen for storage as is, or after purification, the eluate may be subjected to lyophilisation ("freeze-drying") to remove solvent. The resulting liquid or lyophilised product is termed "FSH mutant Bulk".

FSH Formulations

FSH or FSH mutant of the invention or purified according to the method of the invention may be formulated for injection, either intramuscular or subcutaneous, preferably subcutaneous. The FSH mutant formulation may be freeze-dried, in which case it is dissolved in water for injection just prior to injection. The FSH or FSH mutant formulation may also be a liquid formulation, in which case it can be injected directly, without prior dissolution.

The FSH or FSH mutant formulation may be single dose or multiple dose. If it is multiple dose, it should preferably contain a bacteriostatic agent, such as, for example, benzyl alcohol, meta-cresol, thymol or phenol, preferably benzyl alcohol or meta-cresol. Single dose formulations may also comprise a bacteriostatic agent.

The FSH or FSH mutant of the invention may be formulated with known excipients and stabilizers, for example, sucrose and mannitol. It may also comprise an antioxidant, such as methionine. It may further comprise a surfactant, such as TWEEN (preferably TWEEN 20), or Pluronic (preferably Pluronic F68).

A particularly preferred pharmaceutical composition obtainable by the methods of the invention is a freeze-dried formulation, in which a FSH mutant with an alpha subunit according to SEQ ID NO 1 and a beta-subunit according to SEQ ID NO 2 is formulated with sucrose, methionine, Tween 20, $Na_2HPO_4.2H_2O$, $NaH_2PO_4.H_2O$, sodium hydroxide and o-phosphoric acid at a pH of about 7.

In a particularly preferred multidose formulation, FSH produced by the method of the invention is formulated by dissolving it in water for injection with sucrose, phosphate buffer (pH 7), Pluronic F68, methionine and meta-cresol or benzyl alcohol.

Indications

The FSH or FSH mutant of the invention is suitable for use in all treatments where FSH is indicated. It is particularly suited for subcutaneous administration in ovulation induction, controlled ovarian hyperstimulation for assisted reproductive technologies, and in the treatment of oligospermia. It may be used in conjunction with other gonadotrophins, such as LH and hCG. It may also be used with further compounds which augment the response to FSH, such as clomiphene citrate, aromatase inhibitors, such as Anastrozole, Letrozole, Fadrozole and YM-511.

Sequences:
SEQ ID NO. 1: FSH mutant (GM1) α-subunit;
SEQ ID NO. 2: FSH mutant (GM1) β-subunit The expression "recombinant cell" refers to a cell produced by inserting heterologous DNA, including any of the above-mentioned methods of genetic manipulation. Preferably the FSH is produced recombinantly in Chinese hamster ovary (CHO) cells transfected with a vector or vectors comprising DNA coding for the human glycoprotein alpha-subunit and the beta-subunit of FSH. DNA encoding the alpha and beta-subunits may be present on the same or different vectors.

In a preferred embodiment, the FSH or FSH mutant is produced recombinantly in CHO cells, either in a serum or in a serum-free medium.

In a preferred embodiment, the purified FSH or FSH mutant produced according to the method of the invention is suitable for subcutaneous administration, permitting self-administration by the patient.

The expression "crude recombinant FSH or FSH mutant" refers to the cell culture supernatant from recombinant cells expressing FSH, before it has undergone any chromatographic step. The expression encompasses the raw form of the supernatant (as isolated from cells) as well as concentrated and/or filtered and/or ultrafiltered supernatant.

The term "biological activity" in relation to FSH activity, refers to the ability of an FSH mutant formulation to elicit biological responses associated with FSH, such as ovarian weight gain in the Steelman-Pohley assay [Assay of the follicle stimulating hormone based on the augmentation with human chorionic gonadotrophin; Endocrinology; 1953, 53, 604-616], or follicular growth in a female patient. Follicular growth in a female patient can be evaluated by ultrasound, for example, in terms of the number of follicles having a mean diameter of at or about 16 mm on day 8 of stimulation. Biological activity is evaluated with respect to an accepted standard for FSH.

The LH content in an FSH preparation may be measured, for example, using an LH-specific immunoassay, such as the Delfia hLH Spec (Wallac Oy, Turku, Finland).

The term "specific activity", in reference to FSH or the FSH mutant according to the present invention, means the biological activity in IU of the preparation in a recognised biological assay for FSH, such as the Steelman Pohley bioassay [divided by the amount of protein, as determined by an assay for total protein content, such as the Lowry assay [O. H. Lowry, N. J. Rosebrough, A. L. Farr and R. J. Randall (1951) *J. Biol. Chem.* 193: 265; Hartree E. E. (1972). *Anal. Biochem.* 48: 422; J. R. Dulley and P. A. Grieve (1975) *Anal. Biochem.* 64: 136], the Bradford assay [Bradford, M. M. (1976) *Anal. Biochem.* 72, 248], or by absorbance at 280 nm.

The FSH samples may be analysed in respect of their purity at various stages of the procedure using, for example, techniques such as those listed below:

FSH or FSH Mutant Quantification/Free Alpha Subunit/Purity/Oxidised Forms: RP-HPLC As mentioned above, the FSH or FSH mutant is a heterodimeric glycoprotein, composed of an α- and a β-subunit. Some dissociation of the subunits can occur, and this can be monitored by looking at the amount of free α-subunit present in a sample. In addition, the FSH mutant subunits may become oxidised. The oxidised contaminants can be quantified using RP-HPLC, while the free subunits may be assessed using SDS-PAGE.

FSH or FSH Mutant Quantification: Immunoassay

The FSH mutant content in a sample can be determined using an immunoassay specific for the FSH mutant, such as the DELFIA FSH immunoassay.

Total Protein: Bradford Assay, Lowry Assay, Absorbance at 280 Nm

As with any protein preparation, total protein content can be determined using techniques such as a Bradford assay, a Lowry Assay or by absorbance at 280 nm.

Isoforms Pattern: IEF

As mentioned above, the FSH or FSH mutant is a glycoprotein, having multiple oligosaccharide residues attached at various places on both subunits. The oligosaccharide residues may have different degrees of branching and may be capped with sialic acid residues. Sialic acid residues are negatively charged (at neutral pH). Differences in capping leads to heterogeneity, with a mixture of species having different isoelectric points (pI). This can be assessed using a technique that separates based on charge, such as isoelectric focussing (IEF)

Host Cell Protein (HCP)

Host cell protein can be analysed using an ELISA assay. For example, antibodies can be raised to a "mock culture", which is a culture of host cells without FSH gene.

EXAMPLES

The present invention will now be illustrated by means of 2 examples.

Example 1

Step (1): Dye Affinity Chromatography on Blue Sepharose

The FSH mutant starting material for the purification is prepared from cell culture harvests containing recombinant FSH mutant, i.e. the FSH mutant having an alpha subunit according to SEQ ID NO 1 and a beta subunit according to SEQ ID NO 2 was produced recombinantly in CHO cells according to WO 2005/020934. The dye affinity chromatography column (Blue Sepharose FF resin) is first equilibrated with a low conductivity buffer at a pH of 7.0 containing L-methionine. The liquid containing the FSH is then applied directly to the resin. After the load, the unbound material is washed out using equilibration buffer. The FSH is finally eluted by flushing the column with ammonium hydroxide buffer at pH 11.8, containing L-methionine. The elution pool is directly processed to the next step. The step is performed at room temperature.

Step (2): Weak Anion Exchange Chromatography on DEAE Sepharose FF

The Blue sepharose FF eluate from step (1) is loaded onto a DEAE Sepharose FF column equilibrated against an ammonium acetate buffer, pH 8.5, containing ammonium acetate and L-methionine. The unbound material is flushed out with equilibration buffer. The FSH mutant is in the unbound fraction.

Step (3): Hydrophobic Interaction Chromatography (HIC) on Toyopearl Butyl 650M

The Blue Sepharose FF eluate from step (2) is loaded onto a Toyopearl Butyl 650M column equilibrated against a sodium phosphate buffer, pH 7.0, containing ammonium sulfate and L-methionine. The unbound material is flushed out with equilibration buffer. Elution is performed with sodium phosphate buffer pH 7.0 containing ammonium sulphate and L-methionine.

Step (4): Strong Anion Exchange Chromatography on Fractogel EMD TMAE HICAP

The HIC eluate (from step (3)) is loaded on a Fractogel EMD TMAE HICAP column equilibrated against sodium borate buffer, pH 8.5, containing L-methionine. After the load, the column was rinsed with equilibration buffer in order to flush all unbound material. The column was then eluted with Sodium Borate buffer pH 8.5, containing NaCl (to increase conductivity) and L-methionine (as an antioxidant).

Upon following the above procedure, the factor of purification—i.e. the ratio of FSH mutant purity in the purified sample versus the FSH mutant purity in the starting material (crude FSH mutant)—is at about 40.000.

Example 2

Step (0): Capture Step

The FSH mutant starting material for the purification is prepared from cell culture harvests containing recombinant FSH mutant, i.e. the FSH mutant having an alpha subunit according to SEQ ID NO 1 and a beta subunit according to SEQ ID NO 2 was produced recombinantly in CHO cells according to WO 2005/020934.

Clarification

The crude r-FSH mutant was filtered through a depth filter (such as Millipore Millistack filters or equivalent).

The clarified harvest is concentrated on a 8 kDa membrane and capture on Q SFF column.

Step (1): Dye affinity chromatography on Blue Sepharose

The FSH mutant starting material for the purification is prepared from cell culture harvests containing recombinant FSH mutant, i.e. the FSH mutant was produced recombinantly in CHO cells according to WO 2005/020934, either in a serum or in a serum-free medium. The dye affinity chromatography column (Blue Sepharose FF resin) is first equilibrated with a low conductivity buffer at a pH of 7.0 containing L-methionione. The liquid containing the FSH is then applied directly to the resin. After the load, the unbound material is washed out using equilibration buffer. The FSH is finally eluted by flushing the column with ammonium hydroxide buffer at pH 11.8, containing L-methionine. The elution pool is directly processed to the next step. The step is performed at room temperature.

Step (2): Weak Anion Exchange Chromatography on DEAE Sepharose FF

The Blue sepharose FF eluate from step (1) is loaded onto a DEAE Sepharose FF column equilibrated against an ammonium acetate buffer, pH 8.5, containing ammonium acetate and L-methionine. The unbound material is flushed out with equilibration buffer. The FSH mutant is in the unbound fraction.

Step (3): Hydrophobic Interaction Chromatography (HIC) on Toyopearl Butyl 650M The Blue Sepharose FF eluate from step (2) is loaded onto a Toyopearl Butyl 650M column equilibrated against a sodium phosphate buffer, pH 7.0, containing ammonium sulfate and L-methionine. The unbound material is flushed out with equilibration buffer.

Step (3bis) Diafiltration

The FSH mutant from step (3) was concentrated by tangential flow filtration on a 8 KD polyether sulphone membrane. When the retentate reached about half of the initial volume, the material was buffer-exchanged by diafiltration against WFI and then equilibration buffer from the following anion-exchange chromatography

Step (4) Anion-Exchange Chromatography on Fractogel EMD TMAE Hicap Resin

A Fractogel EMD TMAE hicap column was first equilibrated with Sodium Borate buffer, pH 8.5, containing L-methionine. The diluted material (from step (3) was loaded onto the column. The unbound material was flushed out using equilibration buffer. The FSH is eluted from the column increasing the salt concentration in a linear fashion.

Step (5) Nanofiltration

The eluate from the Fractogel EMD-TMAE step (4) was applied directly to a 20 nm nanofiltration device at a pressure of 3 bar under nitrogen. The filtrate is processed to the next step. The operation was performed at 2-8° C.

Step (6) Hydrophobic Interaction Chromatography Step Using a Source 15 HIC Column The filtrate from nanofiltration is adjusted for conductivity and loaded onto a Source 15 HIC column equilibrated against a sodium borate, pH 9.1, containing ammonium sulphate, potassium sulfate and L-methionine. The unbound material is flushed out with equilibration buffer. The FSH is eluted from the column by decreasing the salt content in a stepwise fashion.

A final product of the FSH mutant is obtained whereby the following glycoforms are identified (using an analytical method based on High Pressure Liquid Chromatography):

| | |
|---|---|
| FSH mutant having a triglycosylated beta subunit | 76% |
| FSH mutant having a diglycosylated beta subunit | 24% |

The Purity of the Samples

TABLE 1 purity of the FSH mutant samples after each purification step

| Purification Step | Purity |
|---|---|
| Step (0): Capture Step | 19% FSH FSH determined by RP-HPLC Total protein content determined by Bradford about 1'182'000 ppm HCP |
| Step (1): Dye affinity chromatography on Blue Sepharose FF resin | FSH content determined by RP-HPLC; host cell protein content determined by ELISA Amount of impurity: 586'000 ppm |
| Step (2): Anion-exchange chromatography on DEAE Sepharose FF resin | FSH content determined by RP-HPLC; host cell protein content determined by ELISA Amount of impurity: 3500 ppm |
| Step (3): Hydrophobic Interaction Chromatography on Toyopearl Butyl 650M resin | FSH content determined by RP-HPLC; host cell protein content determined by ELISA Amount of impurity: <1000 ppm |
| Step (4) Anion-exchange chromatography on Fractogel EMD TMAE hicap resin | FSH content determined by RP-HPLC; host cell protein content determined by ELISA |

Biological Activity of FSH Mutant Samples

The biological activity of the purified r-FSH mutant was measured using the Steelman-Pohley ovarian weight gain method. Specific activity was calculated using the biological activity divided by the FSH mutant content as determined by an SE-HPLC method, as described below.

Exemplary values for 2 samples of a final bulk FSH are given in Table 2. The samples were obtained following a method comprising the following steps (0) capture step;
(1) dye affinity chromatography;
(2) weak anion-exchange chromatography;
(3) hydrophobic interaction chromatography (HIC);
(3bis) ultrafiltration;
(4) strong anion exchange chromatography;
(5) Nanofiltration
(6) hydrophobic interaction chromatography (HIC).

Specific activity of the final bulk obtained are typically between 11,000 to 17,000 IU/mg, in particular of 12,000 to 16,000.

TABLE 2

Specific activity of bulk purified r-FSH mutant of the invention

| Analysis | Sample 1 | Sample 2 |
| --- | --- | --- |
| Protein concentration by SE-HPLC (mg/ml) | 0.72 | 0.64 |
| Specific activity (Biological activity/SE-HPLC) | 15'824 IU/mg | 11'914 IU/mg |

The invention claimed is:

1. A method for purifying follicle stimulating hormone (FSH) or an FSH mutant comprising subjecting a liquid sample comprising FSH or an FSH mutant to the following steps wherein the steps are carried out in the order:
  (1) capture step;
  (2) dye affinity chromatography;
  (3) weak anion-exchange chromatography;
  (4) hydrophobic interaction chromatography (HIC);
  (5) ultrafiltration;
  (6) strong anion exchange chromatography;
  (7) nanofiltration; and
  wherein said step of dye affinity chromatography comprises elution of FSH or FSH mutant from the affinity dye with a buffer having a pH of about 9 to about 13.

2. The method of claim 1, wherein the dye affinity chromatography of Step (2) is carried out with a resin having immobilised blue dye.

3. The method of claim 1, wherein the dye affinity chromatography of Step (2) comprises elution of FSH or FSH mutant from said affinity dye using an ammonium hydroxide buffer at a pH of about 9 to about 13 as eluent.

4. The method of claim 1, wherein a resin comprising diethylaminoethyl groups is used for the weak anion exchange chromatography of Step (3).

5. The method of claim 1, wherein the weak anion exchange chromatography of Step (3) is carried out using an ammonium acetate buffer at a pH of about 7.5 to 9.5.

6. The method of claim 1, wherein the hydrophobic interaction chromatography (HIC) of Step (4) is carried out using a resin comprising butyl groups.

7. The method of claim 1, wherein the hydrophobic interaction chromatography of Step (4) is carried out using sodium phosphate/ammonium sulphate with a pH of about 6 to 8 as eluent.

8. The method of claim 1, wherein the resin used for the strong anion exchange chromatography of Step (6) is a resin comprising trimethylaminoethyl groups.

9. The method of claim 1, wherein the step of strong anion exchange chromatography of Step (6) is carried out using sodium borate with a pH of about 7.2 to 9 as eluent.

10. The method of claim 1, wherein the capture Step (1) is carried out using a resin comprising a quarternary amine group.

11. The method of claim 1, wherein said liquid sample further comprises an FSH mutant having a tri-glycosylated beta subunit with the alpha subunit set forth in SEQ ID NO: 1 and the beta subunit set forth in SEQ ID NO: 2, wherein the method comprises a further step of hydrophobic interaction chromatography as the last step, which enriches the liquid sample for the FSH mutant having the tri-glycosylated beta subunit.

12. The method of claim 1, wherein:
  a) eluents used for the purification of said FSH or FSH mutant contain an antioxidant;
  b) buffers used for the purification of said FSH or FSH mutant contain an antioxidant; or
  c) eluents and buffers used for the purification of said FSH or FSH mutant contain an antioxidant.

13. A method for purifying a follicle stimulating hormone (FSH) or an FSH mutant comprising subjecting a liquid sample comprising or an FSH mutant to the following steps wherein the steps are carried out in the order:
  (1) capture step;
  (2) dye affinity chromatography and elution of FSH or FSH mutant from said affinity dye using a buffer having a pH of about 9 to about 13;
  (3) subjecting the FSH or FSH mutant containing eluent of step (2) to weak anion-exchange chromatography and elution of FSH or FSH mutant from said weak anion-exchange resin using a buffer having a pH of about 7.5 to about 9.5;
  (4) subjecting the FSH or FSH mutant containing eluent of step (3) to hydrophobic interaction chromatography (HIC) and elution of FSH or FSH mutant from said hydrophobic interaction resin using a buffer having a pH of about 6 to about 8;
  (5) ultrafiltration of the FSH or FSH mutant containing eluent of step (4);
  (6) subjecting the ultrafiltered FSH or FSH mutant of step (5) to strong anion exchange chromatography and elution of FSH or FSH mutant using a buffer having a pH of about 7.2 to about 9; and
  (7) nanofiltration of the FSH or FSH mutant containing eluent of step (6).

* * * * *

UNITED STATES PATENT AND TRADEMARK OFFICE
CERTIFICATE OF CORRECTION

PATENT NO. : 8,604,175 B2  Page 1 of 1
APPLICATION NO. : 12/092006
DATED : December 10, 2013
INVENTOR(S) : Thierry Ziegler et al.

It is certified that error appears in the above-identified patent and that said Letters Patent is hereby corrected as shown below:

In the Specification

Column 4,
Line 3, "E55NN57T" should read --E55N/V57T--.
Line 7, "E55NN57T" should read --E55N/V57T--.
Line 11, "E55NN57T" should read --E55N/V57T--.

Column 9,
Line 50, "the resin)" should read --the resin).--.

Column 10,
Line 20, "the following characteristics" should read --the following characteristics:--.

Column 12,
Line 27, "$Na_2HPO_4.2H_2O$, $NaH_2PO_4.H_2O$" should read
    --$Na_2HPO_4 * 2 H_2O$, $NaH_2PO_4 * H_2O$--.

Column 13,
Line 63, "(IEF)" should read --(IEF).--.

Column 17,
Line 9, "the following steps" should read --the following steps:--.

In the Claims

Column 20,
Line 28, "comprising or an FSH mutant" should read
    --comprising FSH or an FSH mutant--.

Signed and Sealed this
Twenty-seventh Day of January, 2015

Michelle K. Lee
*Deputy Director of the United States Patent and Trademark Office*